United States Patent [19]

Noack

[11] Patent Number: 4,925,048
[45] Date of Patent: May 15, 1990

[54] FOOT MANEUVERED DISPOSABLE CONTAINER FOR OPERATING ROOM DISCARDS

[75] Inventor: William L. Noack, Camarillo, Calif.

[73] Assignee: Devon Industries, Inc., Chatsworth, Calif.

[21] Appl. No.: 344,618

[22] Filed: Apr. 27, 1989

[51] Int. Cl.$^5$ .......................... B62B 1/00; B65D 81/00
[52] U.S. Cl. ..................................... 220/70; 206/370;
  220/1 T; 220/69; 280/47.3; 280/47.32
[58] Field of Search ................. 206/366, 370; 220/1 T,
  220/69, 70, 83, 404, 904; 280/43.1, 43.24,
  47.131, 47.17, 47.2, 47.3, 47.32

[56] References Cited

U.S. PATENT DOCUMENTS

| | | | |
|---|---|---|---|
| 1,021,679 | 3/1912 | Jansen | 220/69 |
| 1,213,588 | 1/1917 | Cohen | 220/1 T |
| 2,855,061 | 10/1958 | Lilienthal et al. | 280/47.47 |
| 3,618,966 | 11/1971 | Vandervest | 280/43.17 |
| 3,727,546 | 4/1973 | McKinney | 220/404 |
| 3,866,936 | 2/1975 | Hedges | 220/1 T |
| 4,300,696 | 11/1981 | Bryce | 220/1 T |
| 4,420,168 | 12/1983 | Dewing | 220/1 T |
| 4,821,903 | 4/1989 | Hayes | 220/1 T |

FOREIGN PATENT DOCUMENTS 1317039 5/1973 United Kingdom ............. 280/47.32

OTHER PUBLICATIONS

DePuy Catalog "Isolator TM Disposable Kick Bucket", 1988.
Baxter Travenol brochure, "American TM Operating Room Surgical Equipment", 1988.
Blickman Health Industries, Inc. brochure, "Stainless Steel Receptacles", 1988.
Smith * Nephew Wilson brochure "Smith+Nephew", pp. 1 & 14, 1988.
United Metal Fabricators, Inc. brochure, "UMF Custom_Quality", pp. 1 & 21, 1988.
Greystone Medical brochure "Kick & Toss", 1988.

Primary Examiner—Jimmy G. Foster
Attorney, Agent, or Firm—Poms, Smith, Lande & Rose

[57] ABSTRACT

A light weight incineratable plastic material disposable container is disclosed for receiving, storing or counting and subsequent disposal of hospital surgery room discards including medical sponges and has a hollow open top container body or bucket made of a light weight polyethylene material. A single caster means is provided on the bottom of the container body consisting of a single roller mounted at the center of the container bottom for rollably supporting substantially all of the weight of the container and its contents during foot maneuvering of the container on the hospital operating room floor, there being a plurality of skid pads provided about the base on depending therefrom a distance slightly less than that which the single roller depends to provide lateral support as the container tips slightly to accomplish varying three point contacts with the floor.

16 Claims, 2 Drawing Sheets

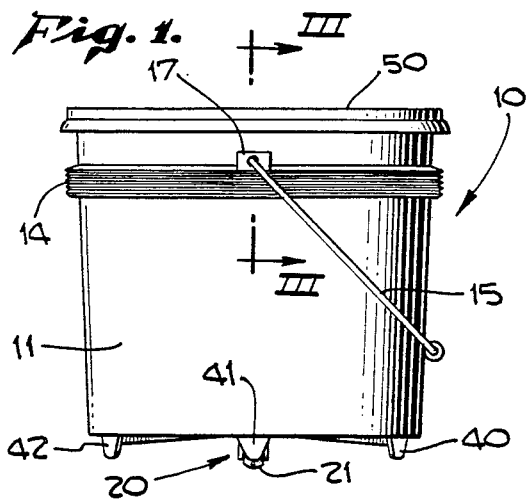
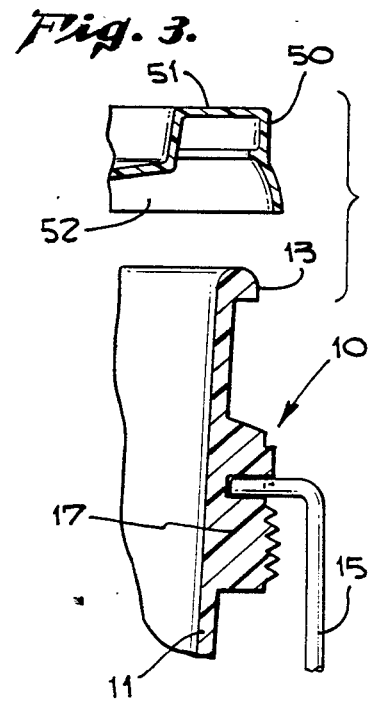
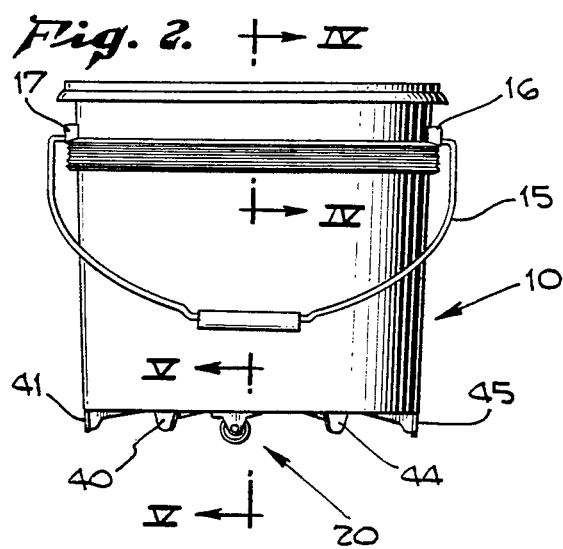
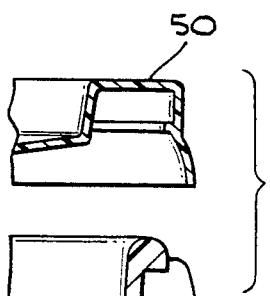
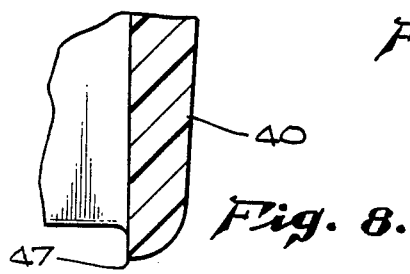
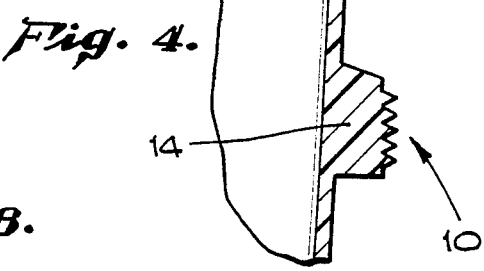

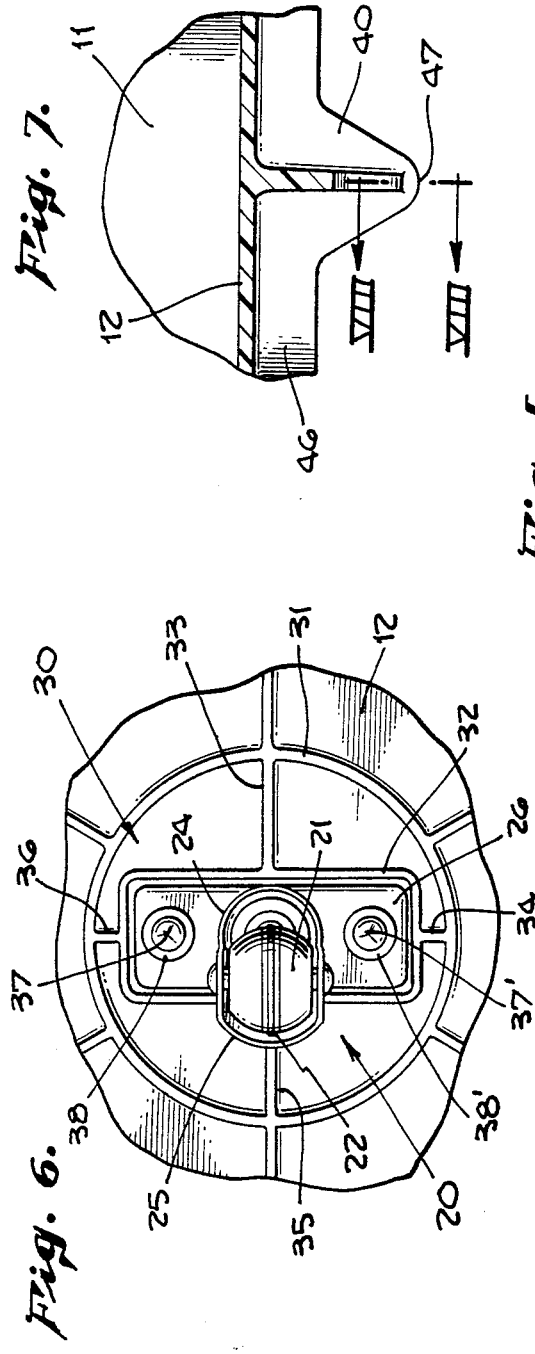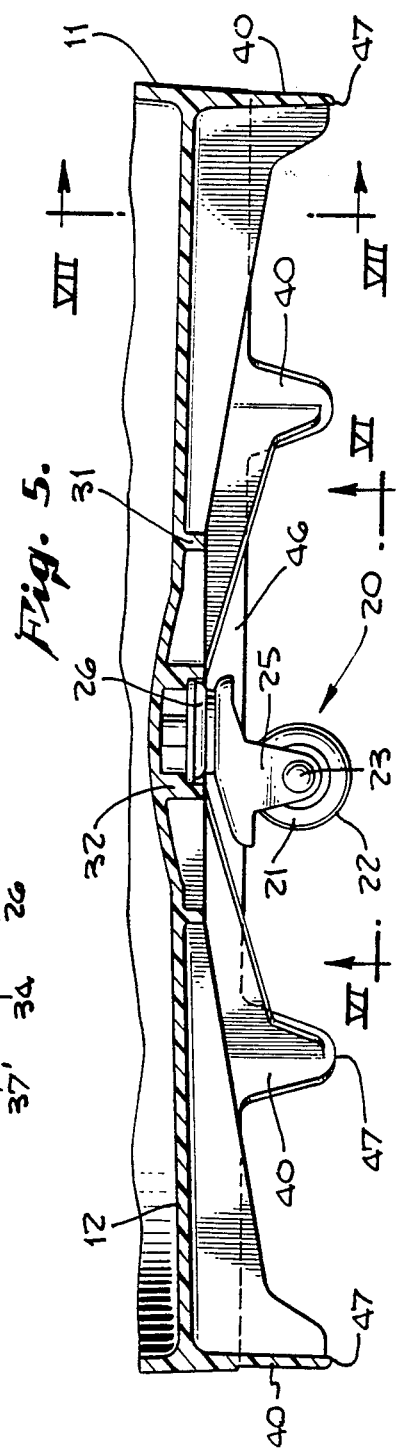

FOOT MANEUVERED DISPOSABLE CONTAINER FOR OPERATING ROOM DISCARDS

INTRODUCTION

This invention relates in general to containers employed in hospital operating rooms for receiving medical discards which need to be stored, counted at the end of the operation and then discarded and more particularly to a foot maneuvered container for such discards which is also disposable.

BACKGROUND OF THE INVENTION

Heretofore it has been common practice in hospital operating rooms to employ a reusable stainless steel container of bucket configuration mounted on a four wheel dolly, somewhat as used in industrial floor moping procedures, to receive medical sponges, packaging from products used during an operation and even occasionally medical sharps and other discards. These "kick buckets" have heretofore been lined with a red bag which received the waste and discards and facilitated disposal of the bag and its contents. The kick bucket is maneuvered about the operating room floor by the doctors or nurses through foot contact to be positioned in different locations for receiving the waste and discards. With disposal of the bag and its contents following any sponge or sharp counting operations, the stainless steel container has been cleaned between procedures and it has been necessary to be quite careful in handling the red bag which contains the waste during the disposal operation. Preferably, such disposal operations include incineration of the disposed items.

In view of the foregoing, it has become apparent that an improved manner of handling operating room waste and discards has been needed and a more secure and certain means for disposal of the waste and contaminated instruments and discards desired particularly with the advent of more contagious type diseases being treated in hospital operating room procedures.

SUMMARY OF THE INVENTION

It is therefore an object of the present invention to disclose and provide a foot maneuvered disposable container for medical operating room discards which is easily maneuvered about the operating room floor by the operating doctor or assisting nurses and or staff which securely retains any sharps, syringes or other instruments which could penetrate a plastic thin walled bag type of disposal means and which, while providing a secure containment for operating room waste and discards can be disposed of, preferably through an incineration process. It is a further object of the present invention to disclose and provide such a container which is easily and inexpensively manufactured so as to be suitable for a one time use and be discarded thereafter.

Generally stated, the present invention in a disposable container for medical operating room discards includes the provision of a container body of bucket like configuration having somewhat tapered, generally cylindrical side walls, a closed base and an open top to receive operating room discards including medical sponges, sharps and the like. A tightly fitting cover is provided so that once the discards have been counted, where counting is required as in the case of sponges and sharps, the container can be covered tightly and disposed of as a single unit.

More specifically, the disposable container of the present invention is provided for easy foot maneuverability about the operating room floor through the provision of a single 360 degree swivel caster means located centrally of the container body or bucket base to support substantially all of the weight of the container and its contents from the central portion of the base to facilitate the maneuverability thereof. Stability for the container with its single centrally located caster means is provided through the provision of a plurality of skid pads formed about the circumference of the container base in a general circular array, the individual skid pads depending from the container base a distance slightly less than that by which the single caster means depends from the base. The container body or bucket thus tips slightly to achieve a three point stable position of rest with most of the weight on the single caster means and a minimal amount of weight on the outboard pair of skid pads providing the three point support. As the bucket is maneuvered about the operating room floor by foot, it assumes different slightly tipped orientations as different adjacent pairs of skid pads provide lateral support to the central single caster means.

More specifically, caster positioning and mounting means are formed integrally of the container base in a central portion thereof for mounting the caster by its support plate in the center of the base with the caster roller depending therefrom. Further, the skid pads are also preferably formed integrally of the container body or bucket. In addition, all of the container and its component parts are preferably made of a high density polyethylene material, including the container body or bucket, the caster means, a pivotally mounted handle and the cover, so that all of the container and its parts can be disposed of through an incineration process after its single use as a hospital room discard receptacle.

It is believed that a better understanding of the present invention in foot maneuvered disposable container, as well as an appreciation of additional objects and advantages thereof would be afforded to those skilled in the art from a consideration of the following detailed description of a preferred exemplary embodiment thereof. Reference will be made to the appended sheets of drawings which will be first briefly described.

DESCRIPTION OF THE DRAWINGS

FIG. 1 is a side elevational view of a preferred exemplary embodiment of foot maneuvered disposable container for medical operating room discards in accordance with the present invention showing a press on cover;

FIG. 2 is a front elevational view of the container of FIG. 1;

FIG. 3 is a detail sectional view of a portion of the container of FIG. 1 taken therein along the plane III—III;

FIG. 4 is a detail sectional view of a portion of the container of FIG. 2 taken therein along the plane IV—IV;

FIG. 5 is a detail section view of the base portion of the container of FIG. 2 taken therein along the plane V—V;

FIG. 6 is a bottom plane view of the central portion of the base of the container of FIGS. 1 through 5 taken in FIG. 5 along the plane VI—VI;

FIG. 7 is a detail section view of a portion of the base taken in FIG. 5 along the plane VII—VII; and FIG. 8 is a detail section view of a portion of the base of FIG. 5 taken along the plane VIII—VIII of FIG. 7.

DETAILED DESCRIPTION OF THE PREFERRED EXEMPLARY EMBODIMENT

The preferred exemplary embodiment of the foot maneuvered disposable container for medical operating room discards, in accordance with the present invention, is seen in side and front elevational views in FIGS. 1 and 2 respectively. The exemplary disposable container, indicated generally at 10, is preferably made of a high density polyethylene material in the form of a bucket having generally cylindrical, but slightly tapering, side walls 11, a closed base 12 and an open top having a surrounding rim 13. The slight tapering of side walls 11 of the container allows for stacking of one upon the other in a nested relationship for ease of storage. A rib 14 is provided about the exterior of side wall 11, as seen in FIGS. 1 and 2, to provide added rigidity to the side wall and can have any desired decorative exterior surface. Handle means are provided in the preferred exemplary embodiment including the handle 15 which is a plastic loop mounted at its opposite ends in handle bosses 16 and 17 formed integrally of the rib 14 and the container side wall 11.

As is particularly contemplated within the present invention, the container is intended to be foot maneuvered about the floor in a hospital surgery room to receive discards such as sponges, sharps, sterile package wrappings and the like. In order to facilitate such foot maneuverability of the container, a single 360 degree swivel caster means, indicated generally at 20, is provided for rollingly supporting the container body or bucket from a central portion thereof. As best seen in FIGS. 1, 2, 5 and 6, the exemplary caster means, indicated generally at 20, includes a roller 21 of generally ball configuration having a roll rib 22 for minimal engagement with the operating floor. Roller 21 is mounted by a shaft 23 to a caster frame 24, having shaft mounting flange 25, which is pivotally mounted by known means to a base plate 26. Caster positioning and mounting means are provided, in accordance with the present invention, preferably as an integral molded portion of base 12 in a central portion thereof as seen in FIGS. 5 and 6, such caster positioning and mounting means, in the exemplary embodiment, is indicated generally at 30 and includes an outer rib 31 of generally circular configuration, inner rib 32 of generally rectangular configuration and interconnecting ribs 33, 34, 35 and 36 running between the inner and outer ribs 31 and 32 respectively. These ribs 31-36 provide a positioning means for the rectangular caster base plate 26. The plate 26 is held to base 12 through the provision of the integrally formed mounting posts 37 and 37' as seen in FIGS. 5 and 6, which pass through mating apertures in the base plate. As the posts are stated by an ultrasonic welder in known manner countersunk holes 38 and 38' are formed and into which melted plastic of the posts floors. The caster means, preferably made entirely of plastic is thereby easily assembled and retained to the integrally provided plastic material positioning and mounting means molded into the container base 12.

In order to provide stability to the container, indicated generally at 10, as it is moved across the operating room floor by simply being kicked along, and as contemplated within the present invention, a plurality of skid pads are formed integrally of the container in a generally circular array about the bottom thereof and depending therefrom as seen in FIGS. 1, 2, 5, 7, and 8. There are preferably six skid pads 40-45 (pad 43 is not seen in FIGS. 1 and 2) which are provided about the circumference of the base integral of a depending skirt 46, as seen in FIGS. 5 and 7, and in equally spaced relationship to provide lateral support to the single caster means indicated generally at 20. Each of such skid pads is provided in depending relation to base 12, as seen in FIG. 7, and is formed with a radiused end surface in a first plane as seen in FIG. 7. In order to reduce the floor contact surface area of each such pad, as pad 40 in FIGS. 7 and 8, the lower end of each pad is also provided with a radiused curved surface 47 in a second plane, as seen in FIG. 8, which is perpendicular to the first plane of FIG. 7. The resultant is an almost line wide edge 47 as seen in FIGS. 5 and 8. Also, as best seen in FIG. 5, the length of the skid pads 40-45, that is the distance which each depends from base 12, is slightly less than the height of the caster means indicated generally at 20 so that the bucket tends to ride with most of its weight on the caster means, indicated generally at 20, and tips slightly onto varying pairs of adjacent ones of said skid pads in varying three point floor contact as the container is kicked about the operating room floor. For example, the container might be resting on roller rib 22 and skid pads 40 and 41 at any given moment and be foot maneuvered to a new location where it might assume a slightly tipped different orientation on roller rib 22 and skid pads 41 and 42, or other variations thereof, there generally being a three point support for the container with such three points comprising two adjacent ones of the plurality of skid pads and the roller rib 22 of roller 21 at any given time.

In the preferred embodiment, the depending height of the caster means, generally at 20 is approximately 0.187 inches greater than the depending height of the skid pads to provide the desired effect wherein substantially all of the weight of the container and its contents are applied to the caster roller with only minimal outer support coming from varying pairs of skid pads.

It is contemplated that during surgery room operations, medical sponges and the like will be deposited in the container through its open top defined by the annular rim 13. At the end of the operation, the sponges may be counted as well as any sharps or other discards normally counted before completion of the surgery room operations. Upon completion of such counting procedures, the contents may be securely retained within the container's "bucket" portion through the application of a cover 50 as illustrated in FIGS. 1 and 2. Cover 50 has a top surface 51 and a surrounding side flange 52 configured, in known manner, to provide for a press on type fit of the cover to the container body or bucket. The container may then be manipulated by handle 15 for appropriate disposal, including the incineration thereof since the preferred polyethylene material for the bucket and all the components, including the handle, cover and caster are all, in accordance with the present invention, suitable for being incinerated as part of an appropriate hospital discard disposal process.

While the present foot maneuvered disposable container is particularly deviced for hospital operating room use, it should be apparent to those skilled in the art that the container of the present invention has many other applications for disposing of biohazardous waste such as labs, research facilities and any other areas where personnel are exposed to infectious waste. There are other applications outside of the medical field such as building maintenance, consumer car wash, production line conveying systems where the foot maneuvered container of the present invention also may be used.

Having thus described a preferred exemplary embodiment of the foot maneuvered disposable container for medical operating room discards in accordance with the present invention, it should be appreciated by those skilled in the art that various modifications, adaptations and alternative embodiments thereof may be made within the scope of the present invention which is defined by the following claims.

We claim:

1. A foot maneuvered disposable container comprising:
   a bucket having side walls, a closed base and an open top;
   a single caster means for rollingly supporting said bucket, said caster having a roller depending from a support frame;
   caster positioning and mounting means formed integrally of said base in a central portion thereof for mounting said caster frame in the center of said base with said roller depending therefrom; and
   a plurality of skid pads formed integrally of said bucket and provided in a generally circular array about the bottom of said bucket, each of said pads depending from said bucket to provide lateral support for said bucket relative said caster, whereby said bucket may be foot maneuvered on said single caster without said bucket tipping over.

2. The foot maneuvered disposable container of claim 1 wherein said container is intended to receive medical operating room discards, or the like, and is provided with a press on cover to facilitate the disposal of said container and its contents.

3. The foot maneuvered disposable container of claim 1 wherein said plurality of skid pads depend a first given distance below said base which is slightly less than a second given distance which said roller depends from said base whereby the majority of the weight of said container and its contents is supported by said single caster.

4. The foot maneuvered disposable container of claims 1 or 3 wherein said skid pads are spaced circumferentially about said base whereby said bucket is normally supported by two adjacent ones of said tabs and said roller in a three point support.

5. The foot maneuvered disposable container of claim 1 wherein each of said tabs is provided with a radiused end surface to reduce the extent of contact between an end of such tab and said floor.

6. The foot maneuvered disposable container of claim 5 wherein said radiused end surface has a first radius generated surface in a first vertical plane and has an end radiused surface generated by a second radius lying in a second vertical plane perpendicular to said first plane whereby an edge point is presented to the floor by the end of said tab.

7. The foot maneuvered disposable container of claim 1 wherein said caster has a base plate pivotally mounting said frame and said caster positioning and mounting means compress a rim formed integrally of said base and configured to surround and receive said base plate in a snug fit thereto.

8. The foot maneuvered disposable container of claim 7 wherein said caster positioning and mounting means further comprises:
   one or more mounting parts formed integrally of said base for protruding through mating apertures in said base plate, the outer ends of said parts being mechanically spread to retain said plate to said base.

9. The foot maneuvered disposable container of claim 1 wherein:
   handle means are provided on said bucket for manually maneuvering said bucket.

10. A container comprising:
    a hollow open top container body;
    a 360 degree swivel caster means on the bottom of said body consisting of a single 360 degree swivel roller mounted at the center of said bottom for rollably supporting said body and its contents; and
    a plurality of skid pads provided about and spaced from said caster means on the bottom of said body to give antitipping stability to said single roller supported body.

11. The container of claim 10 wherein mounting means are formed integrally of said base for mounting said caster means to said base, said mounting means including ribs formed in said base to position said caster means in a central portion of the underside of said base and one or more depending, integrally formed mounting posts for engaging and holding said caster means to said base.

12. The container of claim 10 wherein said skid pads are provided as six individual pads formed integrally of said container body and equally spaced about the circumference of said base whereby said container is normally resting primarily on said roller and partially on two adjacent ones of said tabs in a three point stance.

13. The container of claim 11 wherein said pads are each provided with end surfaces generated by radius curved surfaces in two planes perpendicular to each other for a reduced ground contact effect for said tabs.

14. The container of claim 10 wherein:
    handle means are provided for manual movement of said container body and cover means are provided for closing said body preparatory to disposal thereof, said handle means and cover being made of a light weight incineratable plastic material.

15. The container of claim 10 wherein said container body is provided as a one piece molded body of high density polyethylene material and said skid pads are formed integrally of said body and of said material.

16. The container of any of claims 10 through 14 wherein said container is made of a light weight incineratable plastic material for receiving, storing and disposing of hospital surgery room discards including medical sponges and the like and wherein said body, caster means and skid pads are all made of a light weight incineratable plastic material.

* * * * *